US00PP28745P3

(12) United States Plant Patent
O'Connell

(10) Patent No.: US PP28,745 P3
(45) Date of Patent: Dec. 5, 2017

(54) ***ECHEVERIA* PLANT NAMED 'GALAXY BLUE'**

(50) Latin Name: ***Echeveria* hybrid**
Varietal Denomination: Galaxy Blue

(71) Applicant: Renee O'Connell, Escondido, CA (US)

(72) Inventor: Renee O'Connell, Escondido, CA (US)

(73) Assignee: Altman Specialty Plants, Inc, Vista, CA (US)

( * ) Notice: Subject to any disclaimer, the term of this patent is extended or adjusted under 35 U.S.C. 154(b) by 55 days.

(21) Appl. No.: 14/756,705

(22) Filed: Oct. 1, 2015

(65) Prior Publication Data

US 2017/0099761 P1 Apr. 6, 2017

(51) Int. Cl.
*A01H 5/02* (2006.01)

(52) U.S. Cl.
USPC ..... Plt./373

(58) Field of Classification Search
USPC ..... Plt./373, 263.1
See application file for complete search history.

*Primary Examiner* — Keith Robinson
(74) *Attorney, Agent, or Firm* — Cassandra Bright

(57) ABSTRACT

A new and distinct *Echeveria* cultivar named 'Galaxy Blue' is disclosed, characterized by concentric rosettes comprised of an abundance of undulate, icy blue leaves tipped with crimson. Further, the new cultivar 'Galaxy Blue' freely offsets, enabling increased and faster propagation in the commercial nursery. The new cultivar 'Galaxy Blue' exhibits moderately fast, robust growth, which, in combination with freely offsetting results in attractive clusters at an early age, thereby enhancing production intervals. The new variety is an *Echeveria*, part of the Crassulaceae complex that includes *Aeonium, Crassula, Graptopetalum, Pachyphytum, Sedum* and others. *Echeveria* is a popular genus, typically produced as container plants for the patio or as landscape plants, as a variety of ornamental purposes.

3 Drawing Sheets

Latin name of the genus and species: *Echeveria* hybrid. Variety denomination: 'GALAXY BLUE'.

BACKGROUND OF THE INVENTION

The new cultivar, *Echeveria* 'Galaxy Blue', is a product of a planned breeding program. The new variety originated from a cross pollination of the unpatented proprietary seed parent, *Echeveria* 'MI-9' with the pollen parent, the unpatented, proprietary *Echeveria* hybrid referred to as 'GLAV07'. The cross pollination was made during May 2011 in Vista, Calif., at a commercial greenhouse. *Echeveria* 'Galaxy Blue', was discovered by the inventor, Renee O Connell, in February, 2012, in Vista, Calif., at a commercial greenhouse.

Asexual reproduction of the new cultivar 'Galaxy Blue' was first performed in Vista, Calif., at a commercial greenhouse, by terminal vegetative cuttings in April, 2012. *Echeveria* 'Galaxy Blue' has since produced multiple generations and has shown that the unique features of this cultivar are stable and reproduced true to type.

SUMMARY OF THE INVENTION

The cultivar 'Galaxy Blue' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'GALAXY BLUE'. These characteristics in combination distinguish 'GALAXY BLUE' as a new and distinct *Echeveria* cultivar:

1. *Echeveria* 'Galaxy Blue' exhibits very concentric, flattened rosettes with an abundance of undulate, icy blue leaves, tipped in crimson.
2. Additionally, *Echeveria* 'Galaxy Blue' exhibits moderately fast growth, in combination with early, profuse offsetting, producing morphologically attractive icy blue clusters.
3. *Echeveria* 'Galaxy Blue' is easily and rapidly propagated due to robust growth, and prolific offsetting, enhancing production times in the commercial nursery.

PARENTAL COMPARISON

Plants of the new cultivar 'Galaxy Blue' can be compared to plants of the seed parent *Echeveria* 'MI-9', and are similar in most horticultural characteristics. However, the new cultivar 'Galaxy Blue' forms a larger rosette than does the seed parent *Echeveria* 'MI-9', and the new cultivar 'Galaxy Blue' produces more offsets than does the seed parent *Echeveria* 'MI-9'. The new cultivar 'Galaxy Blue' grows much faster and much more robustly than does *Echeveria* 'MI-9', thereby reducing production times measurably, as compared to *Echeveria* 'MI-9'. *Echeveria* 'Galaxy Blue' differs from the seed parent 'MI-9' in that it forms low-growing rosettes of icy blue, undulate leaves, whereas the seed parent 'MI-9' produces taller rosettes that are comprised of rounded, chunky blue leaves. Additionally, the new cultivar 'Galaxy Blue' produces more inflorescences and more complex inflorescences that the simple inflorescences produced by the seed parent 'MI-9'.

Plants of the new cultivar 'Galaxy Blue' can be compared to plants of the pollen parent *Echeveria* 'GLAV07', and are similar in most horticultural characteristics. However, the new cultivar 'Galaxy Blue' forms much more concentric, geometric rosettes than the lax, non-concentric rosettes formed by *Echeveria* 'GLAV07'. Additionally, the new cultivar 'Galaxy Blue' is icy blue in color, whereas the pollen parent *Echeveria* 'GLAV07' is a pallid lavender. The new cultivar 'Galaxy Blue' is freely offsetting, as compared to the sparse offsetting of the pollen parent *Echeveria* 'GLAV07'.

COMMERCIAL COMPARISON

The new cultivar 'Galaxy Blue' can be compared to the, unnamed *Echeveria peacockii*. Plants of *Echeveria peacockii* are similar to plants of the new cultivar 'Galaxy Blue' in most horticultural characteristics. However, the new cultivar 'Galaxy Blue' displays a more concentric, low growing morphology than does *Echeveria peacockii*. In addition, the new cultivar 'Galaxy Blue' forms a more concentric rosette than does *Echeveria peacockii*, producing a more aesthetic rosette. In addition, the new cultivar 'Galaxy Blue' produces rosettes with an abundance of leaves, creating a fuller appearance, as compared with *Echeveria peacockii*. Plants of the cultivar 'Galaxy Blue' offset more profusely than *Echeveria peacockii*, enhancing the propagation rate, and producing a morphologically aesthetic cluster.

The new cultivar 'Galaxy Blue' can be compared to the unpatented commercial variety *Echeveria* 'Perle von Nurnberg'. Plants of *Echeveria* 'Perle von Nurnberg' are similar to plants of the new cultivar 'Galaxy Blue' in most horticultural characteristics. However, the cultivar 'Galaxy Blue' displays a more concentric rosette than is displayed by *Echeveria* 'Perle von Nurnberg'. In addition, the new cultivar 'Galaxy Blue' produces rosettes with an abundance of leaves, creating a much more full appearance, whereas *Echeveria* 'Perle von Nurnberg' has less leaves per rosette. The new cultivar 'Galaxy Blue' offsets profusely, enhancing propagation times, and producing a more aesthetic plant, whereas *Echeveria* 'Perle von Nurnberg' rarely offsets.

BRIEF DESCRIPTION OF THE PHOTOGRAPHS

The accompanying photographs in FIG. 1 through FIG. 3 illustrate in full color typical plants of 'GALAXY BLUE' grown in a greenhouse in Vista, Calif. Age of the plants is approximately 1 year. The photographs were taken using conventional techniques and equipment. While the colors in these photographs may display variances of color as compared to the living cultivar, due to LRV (light reflectance value), they are as accurate as possible using conventional photographic techniques. Colors in the photographs may appear to differ slightly from the color values cited in the botanical description, which accurately describe the colors of the new *Echeveria* plant. The following photographs depict plants grown under natural light conditions of 2500-4000 foot-candles. Temperatures ranged from −1° C. to 29° C. night and day. No artificial light, photoperiodic treatments or chemical treatments were given to the plants.

DETAILED BOTANICAL DESCRIPTION

Figure 1:
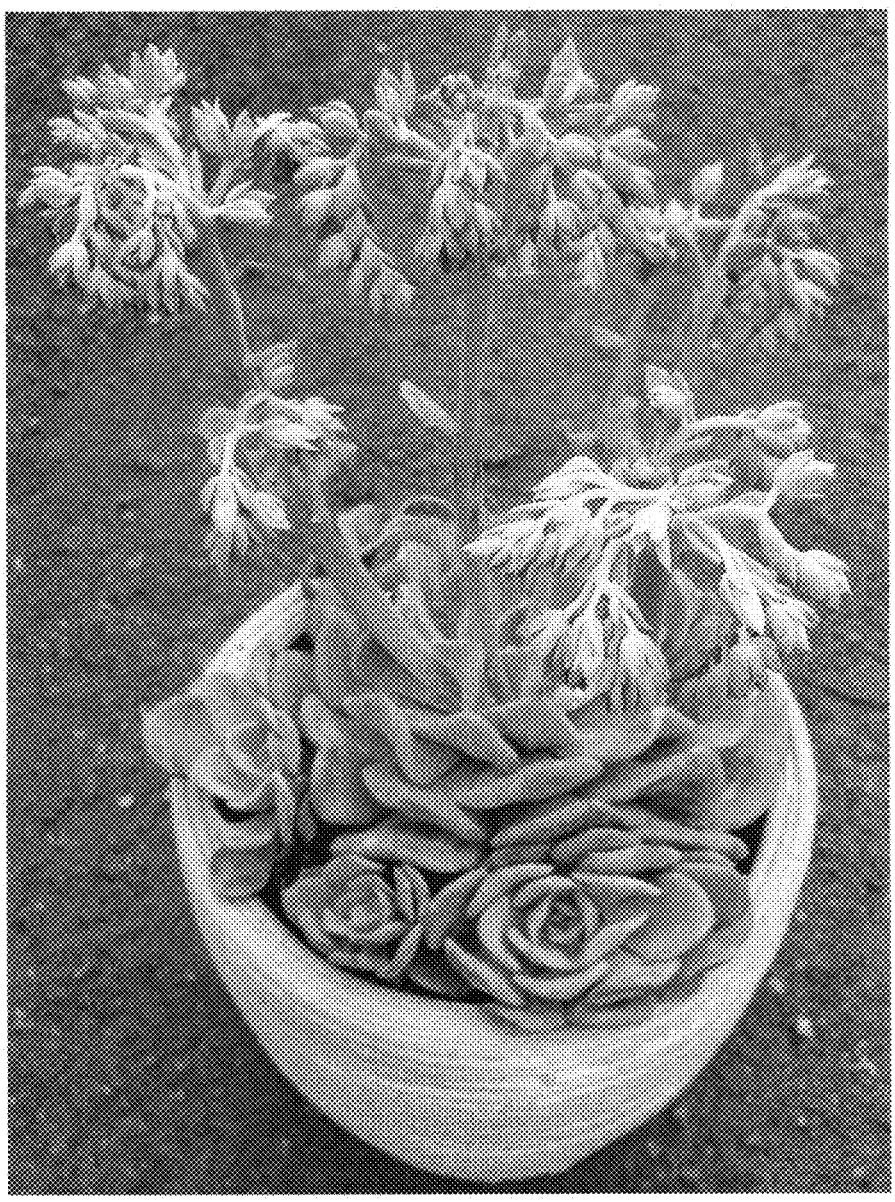
FIG. 1 illustrates in full color a rosette with inflorescences typical of plants of *Echeveria* 'Galaxy Blue' grown in a greenhouse in Vista, Calif.
Figure 2:
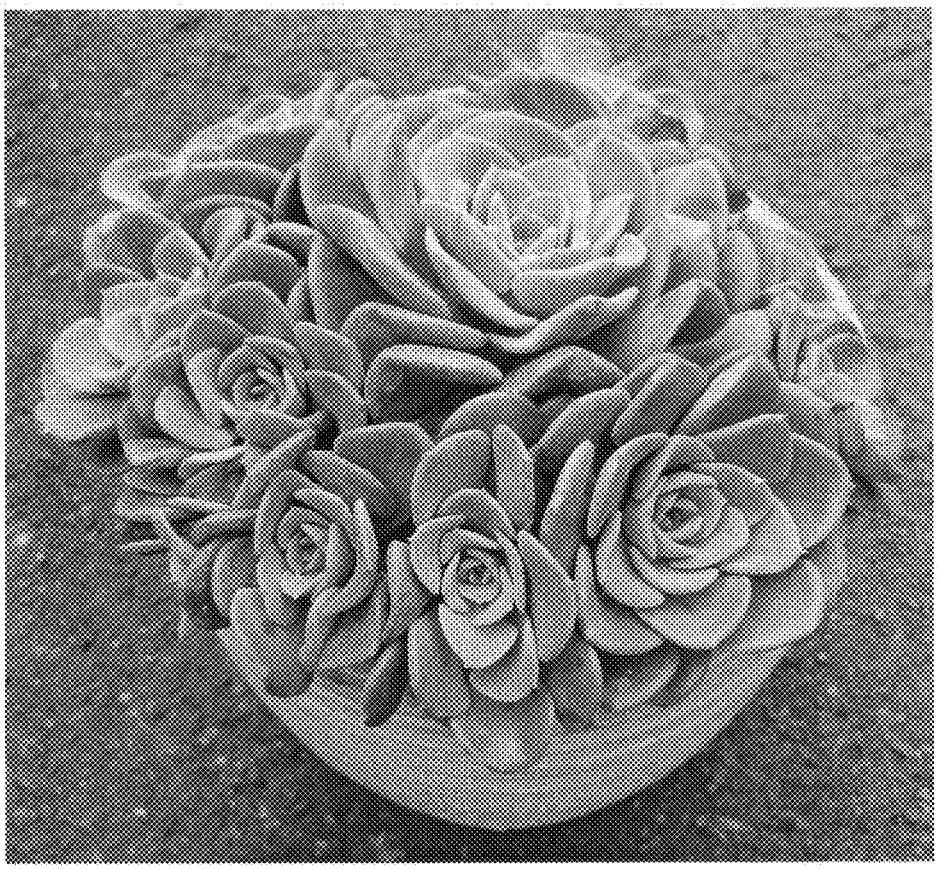
FIG. 2 illustrates in full color an offsetting rosette typical of plants of *Echeveria* 'Galaxy Blue' grown in a greenhouse in Vista, Calif.
Figure 3:
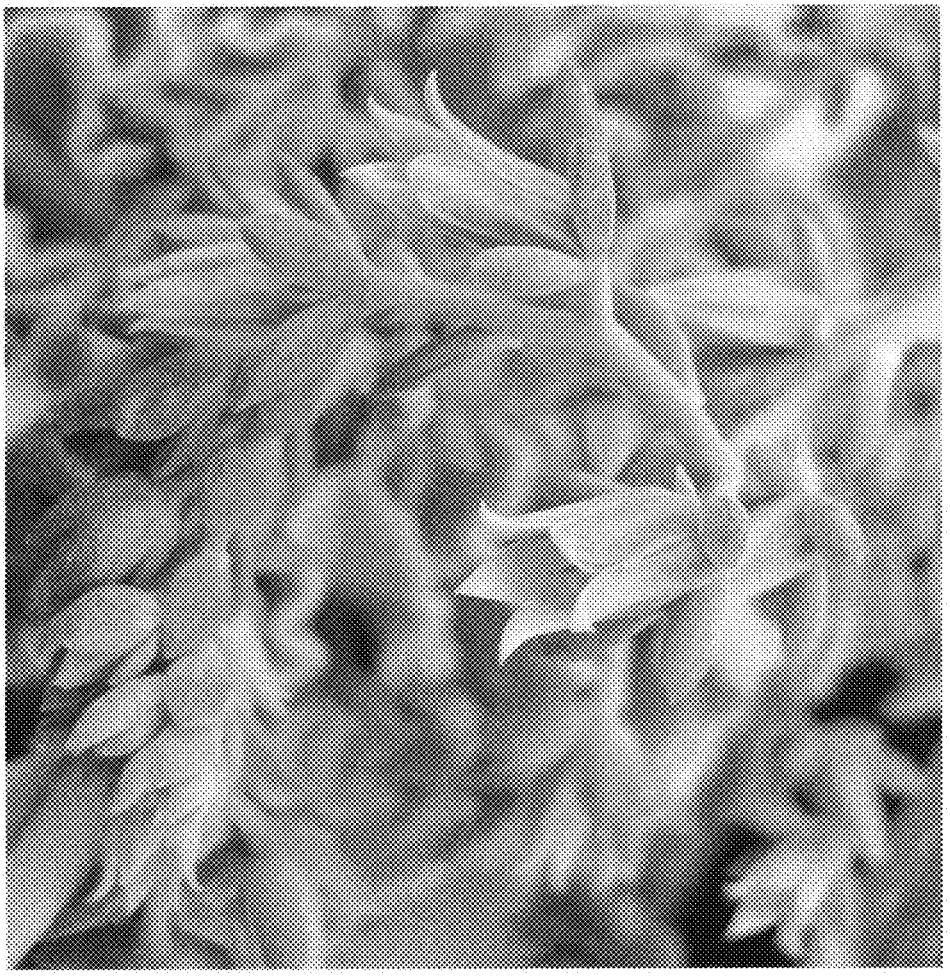
FIG. 3 illustrates in full color a close-up of the flower typical of plants of *Echeveria* 'Galaxy Blue' grown in a greenhouse in Vista, Calif.

In the following description, color references are made to the Pantone Process Color System Guide, Pantone CYMK, 2014, except where general terms of ordinary dictionary significance are used. The following observations and measurements describe 'Galaxy Blue' plants in a commercial greenhouse in Vista, Calif. Temperatures ranged from −1° C. to 29° C. night and day. No artificial light, photoperiodic treatments or chemical treatments were given to the plants. Natural light conditions were approximately 2500 to 4000 fc of light. Measurements and numerical values represent averages of typical plant types.

Botanical classification: *Echeveria* hybrid 'GALAXY BLUE'.

PROPAGATION

Type of propagation typically used: Terminal vegetative cuttings. 'Galaxy Blue' can also be propagated from leaf cuttings and tissue culture.

Time to initiate roots: About 10 days at approximately 24° C.

Root description: Fibrous.

PLANT

Age of plant described: Approximately 4 months.

Container size of the plant described: 14 cm.

Growth habit: Acaulescent rosette plant.

Height: Approximately 5 cm to top of highest leaf. Approximately 12.5 cm. to top of highest inflorescence.

Plant spread: Approximately 18 cm.

Growth rate: Moderately fast.

Branching characteristics: Freely off-setting from base.

FOLIAGE:

Leaf:

*Arrangement*.—Rosulate.

*Average length*.—Approximately 3.5 to 4 cm. Longest 5.0 cm.

*Average width*.—2.2 cm.

*Widest width*.—Approximately 3.25 cm.

*Width at base*.—0.8 cm.

*Shape of blade*.—Obovate.

*Apex*.—Rounded.

*Base*.—Tapered.

*Margin*.—Entire. Somewhat undulate over time.

*Texture of top surface*.—Glabrous, somewhat glaucous.

*Texture of bottom surface*.—Glabrous, glaucous.

*Quantity of leaves per plant*.—Approximately 62.

*Color*.—Young foliage upper side, middle of leaf Near S 133-5 Pantone. Young foliage, upper side, near apex: Near S 133-5 Pantone. Young foliage, upper side, apical margin: Near S 289-6 Pantone. Young foliage upper side, near base: Near S 305-9 Pantone. Young foliage, under side, near apex: Near S 325-5 Pantone. Young foliage, underside, near base: Near S 300-8 Pantone. Mature foliage upper side: Near S 133-3 Pantone. Mature foliage, upper side, near apex: Near S 327-5 Pantone. Mature foliage, upper side, glaucous layer: Near S 245-7 Pantone.

*Venation*.—There is no visual appearance of venation.

FLOWER

Natural flowering season: April, May and June.

Inflorescence type and habit: Erect paniculate-cymose.

Rate of flower opening: 1 flower opens every 2-3 days, depending upon ambient temperatures.

Flower longevity on plant: 3-4 days, depending upon ambient conditions.

Quantity of flowers: 41.

Total inflorescence size:

*Height*.—Approximately 21 cm.

*Width*.—Approximately 9.5 cm.

Corolla:

*Arrangement*.—Pentagonal.

*Size*.—

*Length*.—Approximately 1.35 cm.

*Width*.—Approximately 0.5 cm at widest point.

*Lobe length*.—Approximately 1.35 cm.

*Lobe width*.—Approximately 0.2 cm.

*Petal texture*.—Interior and exterior surfaces glabrous.

Petals:

*Color*.—When opening: Outer surface: Near S 73-5 Pantone. Inner surface: Near S 73-6 Pantone. Fully opened: Petal color, outer surface: Near S 107-3 Pantone & S 107-4 Pantone. Petal color, outer surface, apex: Near S 56-6 Pantone. Petal color, inner surface, near base: Near S 148-4 Pantone. Color Changes when Aging: Near S 124-5 Pantone.

Bud: (near opening):

*Shape*.—Conical tubular.

*Length*.—Approximately 0.6 cm.

*Diameter*.—Approximately 0.3 cm.

*Color*.—Between S 18-7 and S 18-8 Pantone.

Sepals:

*Margin*.—Entire.

*Shape*.—Cylindrical.

*Apex*.—Acute.

*Texture*.—Glabrous.

*Color*.—Outer corolla: Near P 329-3 Pantone. Inner corolla, P 329-1 Pantone.

*Length*.—Approximately 4 mm.

*Width*.—Approximately 3 mm.

Pedicels:

*Length*.—Approximately 0.7 cm.

*Width*.—Approximately 0.2 cm.

*Strength*.—Strong, flexible.

*Texture*.—Glabrous.

*Color*.—Near S 147-7 Pantone.

*Fragrance*.—None detected.

REPRODUCTIVE ORGANS

*Stamens*.—(Androecium). Number: Average 10. Filament Length: Approximately 0.4 cm. Filament Color: Near S 5-9 Pantone. Anther length: 0.125 cm. Anther Color: Near S 9-6 U Pantone. Anther Shape: Oblong. Pollen Color: Near S 5-5 Pantone. Pollen Quantity: Moderate.

*Pistil*.—(Gynoecium). Number: Average 5. Length: Approximately 0.55 cm. Style Color: Near S 92-5 Pantone. Stigma: Shape: Round. Color: Between S 92-3 Pantone and P 92-4 U. Ovary Color: Near S 32-8 Pantone.

OTHER CHARACTERISTICS

Fruits and seeds: Typical to Genus. Minute, approximately 1 mm dry seeds. Colored between black and brown, too small to accurately measure with color chart.

Temperature tolerance: Tolerates temperatures from approximately −2 C to at least 35 C.

Disease/pest resistance: Neither resistance or susceptibility to normal diseases and pests of *Echeveria* has been observed.

Drought tolerance: Tolerates at least 3 weeks of high temperatures without supplemental water, showing no serious damage to plant.

What is claimed is:

1. A new and distinct cultivar of *Echeveria* plant named 'GALAXY BLUE' as herein illustrated and described.

* * * * *